US007112688B1

(12) United States Patent
Tysinger et al.

(10) Patent No.: US 7,112,688 B1
(45) Date of Patent: *Sep. 26, 2006

(54) SOYBEAN OIL PROCESS

(75) Inventors: Jerry E. Tysinger, Warsaw, NC (US); Robert B. Dawson, Warsaw, NC (US)

(73) Assignee: Carolina Soy Products, LLC, Warsaw, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/201,948

(22) Filed: Aug. 11, 2005

(51) Int. Cl.
*C07C 53/00* (2006.01)

(52) U.S. Cl. ....................................... 554/100; 426/489

(58) Field of Classification Search ................ 554/100; 426/489

See application file for complete search history.

(56) References Cited

U.S. PATENT DOCUMENTS

| | | | | |
|---|---|---|---|---|
| 4,049,686 | A | | 9/1977 | Ringers et al. |
| 4,089,880 | A | | 5/1978 | Sullivan |
| 4,255,346 | A | | 3/1981 | Kock |
| 4,267,118 | A | | 5/1981 | Trueblood et al. |
| 4,515,726 | A | | 5/1985 | Sullivan |
| 4,584,141 | A | | 4/1986 | Paulitz et al. |
| 4,698,185 | A | | 10/1987 | Dijkstra et al. |
| 4,808,426 | A | | 2/1989 | Strop et al. |
| 4,944,954 | A | | 7/1990 | Strop et al. |
| 5,225,230 | A | * | 7/1993 | Seaman et al. ............. 426/634 |
| 5,239,096 | A | | 8/1993 | Rohdenburg et al. |
| 5,362,893 | A | | 11/1994 | Muylle et al. |
| 5,516,924 | A | | 5/1996 | van de Sande et al. |
| 5,981,781 | A | | 11/1999 | Knowlton |
| 6,033,706 | A | | 3/2000 | Silkeberg et al. |

* cited by examiner

*Primary Examiner*—Deborah D. Carr
(74) *Attorney, Agent, or Firm*—MacCord Mason PLLC

(57) ABSTRACT

A solvent extraction free, caustic refining free, process for producing refined soybean oil from soybeans includes the steps of heating cleaned, cracked and dehulled soybeans at a temperature of from 220° F. to 600° F. for from 45 to 60 minutes; mechanically pressing the heated soybeans to separate soybean oil; and heating the extracted oil at a temperature of from about 350° F. to about 500° F. under a vacuum to remove free fatty acids from the soybean oil.

13 Claims, No Drawings

SOYBEAN OIL PROCESS

BACKGROUND OF THE INVENTION (1) Field of the Invention

The present invention relates generally to a process for extracting and refining vegetable oils and to the resultant product, and in particular to the production by a combination of mechanical extraction and physical refining of non-hydrogenated soybean oil having an acceptable frylife similar to that of partially hydrogenated soybean oil.

(2) Description of the Prior Art

Soybean oil production involves several steps that are necessary to render the soybean oil suitable for human consumption. These production steps may be broadly characterized as 1) soybean preparation, 2) oil extraction, and 3) oil refining. Soybean preparation generally includes the steps of cleaning, drying, cracking, and dehulling.

The great majority of commercial soybean oil production processes extract or separate the oil from the soybean meal by a process known as solvent extraction. In the solvent extraction process, the prepared beans are first flaked to provide a large surface area. A solvent, commonly hexane, is then pumped through the soybean flakes to dissolve the oil in the hexane, separating approximately 99.5% of the oil from the meal. The hexane is then separated from the oil and recycled.

The crude oil resulting from the solvent extraction must then be subjected to additional treatments, collectively called "refining", to remove various materials in order for the oil to be suitable for consumption. These materials include hydratable and non-hydratable phospholipids, free fatty acids, and various color and flavor components. Crude soybean oil contains phosphorous compounds called hydratable phospholipids, and small amounts of calcium and magnesium that complex with a portion of the phospholipids to form non-hydratable phospholipids. Hydratable phospholipids are normally removed by a process known as "degumming", in which the oil is agitated or otherwise intimately combined with water to precipitate gums from the oil. The gums are then removed by centrifugation.

These precipitated gums can be used as a feed additive, or evaporated to remove moisture. The end product, lecithin, has various end uses such as in food emulsifiers. The degummed oil is dried under vacuum to remove any water. Removal of non-hydratable phospholipids is considerably more difficult and expensive, requiring further chemical treatment, typically chemical refining, to break the chemical bonds between the calcium or magnesium ions and the phospholipids, followed with extensive bleaching of the oil.

In most processes, free fatty acids are removed from the oil by a process known as caustic refining, also called chemical or alkali refining, in which the oil is mixed with a caustic material, such as sodium or potassium hydroxide, which undergoes a saponification reaction with the acids, forming soaps that are then removed by centrifugation. Non-hydratable phospholipids are removed along with the free fatty acids. Chemical refining soybean oil is an expensive process, requiring a large investment in capital equipment. In addition, a significant quantity of the oil is captured by the soaps, adversely affecting oil yield. Also, the caustic refining process produces soapstock, which has little commercial value, and is difficult to dispose of without environmental problems.

Conventional refining processes also involve some bleaching of the soybean oil to remove color pigments that adversely affect the color of the oil. Finally, chemicals that add flavors to the oil are removed by a process known as "deodorization", which is essentially a form of physical distilling, in which the oil is subjected to high temperatures under a vacuum for a short period of time, which is sufficient to remove the flavor-causing components, but insufficient to break down non-hydratable phospholipids.

A major use of soybean oil is in deep frying of foods, such as chicken, fish, french fries, etc., either in the production of pre-cooked packaged foods, or in the preparation of foods for on-premise or carry-out consumption in restaurants and other commercial establishments. In deep frying, a container or vat is filled with cooking oil that is heated to a frying temperature, normally around 350° to 375° F. The uncooked food is then immersed in the hot oil for a sufficient time to effect the desired cooking, and then removed for serving or packaging.

Some of the oil in the vat is lost during cooking due to absorption and evaporation. The oil is replenished by adding fresh oil to the oil remaining in the vat, and the oil is reused. This procedure is repeated until the oil becomes unusable, as indicated by darkening of the oil and the food cooked in the oil, and/or by the observance of an undesirable taste or appearance in the food being cooked.

Non-hydrogenated soybean oil produced by solvent extraction and caustic refining is unsuitable for use in commercial frying operations due to its limited frylife. Such oil has a maximum frylife of only about 4–5 fry cycles, a cycle being the frying of one batch of food. Replacement of the oil at this frequency is uneconomical. In order to extend the frylife of soybean oil to a commercially acceptable number of fry cycles, preferably at least about 30 fry cycles, refined soybean oil is normally at least partially hydrogenated. Hydrogenation of solvent extracted, caustic refined soybean oil reduces the percentage of C 18:3 acids. It is commonly believed that the presence of C 18:3 acids contribute to the rapid deterioration, and thereby limited frylife, of solvent extracted, caustic refined soybean oil.

Saturation or hydrogenation of C 18:3 acids, however, reduces the healthful properties of soybean oil. Therefore, attempts have also been made to reduce the C 18:3 or linolenic acid content of soybean oil by genetically modifying or selective breeding the soybean, thereby enabling the production of non-hydrogenated soybean oil having a C 18:3 content of significantly less than the 6–8% by weight C 18:3 acids, based on the total content of free fatty acids, found in conventional soybeans. U.S. Pat. No. 5,981,781 to Knowlton, issued Nov. 9, 1999, is an example of these generically modified soybeans. This approach, to date, has met with at most limited success.

Commonly assigned U.S. Pat. No. 6,511,690, issued Jan. 28, 2003 and U.S. Pat. No. 6,753,029, issued Jun. 22, 2004, (herein the "Tysinger et al. patents"), both patents incorporated herein in their entireties by reference, describe an improved refining process combining mechanical extraction with physical refining. As noted in the Tysinger et al. patents, mechanical oil extraction and physical refining were previously known separately, but had not been used in combination, and these resultant properties of the resultant oil had not been appreciated.

In the prior art mechanical oil separation process known as expelling, dehulled beans are extruded through a screw press to frictionally heat the beans and rupture the oil cells. Within the screw press, the beans are subjected to high pressures and frictionally-generated high temperatures for a short period. The crushed, oil-containing meal is then pressed to separate most of the oil from the meal. This process has been rarely used to process soybeans due to the fact that about 25% of the soybean oil is left in the meal.

Physical refining has been used for oils that are naturally low in non-hydratable phospholipids, such as lauric oils, particularly palm oil. In physical refining, the oil is vacuum distilled at high temperatures, e.g., from about 450° F. to about 500° F., to separate more volatile components from the oil. This process is used to remove various flavor components, and will also remove free fatty acids. However, the process alone is not viable for removing free fatty acids from oils such as soybean oil, which contains higher levels, i.e., more than 20 ppm based on elemental phosphorous content, of non-hydratable phospholipids. The high temperatures required for physical refining tend to break down the non-hydratable phospholipids that are present in the soybean oil, producing chemical compounds that cause an unacceptable flavor and color.

In the process described in the Tysinger et al. patents, soybean oil is mechanically separated from prepared soybeans by first rapidly heating the beans to a temperature of from about 300° F. to about 370° F., preferably from about 315° F. to about 335° F., followed by mechanically pressing the oil from the beans. Desirably, the beans are crushed during or after heating to assist in freeing the oil from the remainder of the soybeans, i.e., the meal. After degumming and bleaching, the soybean oil is physically refined to remove free fatty acids and flavor components by heating the oil in a distillation column to a temperature of from about 450° F. to about 500° F., and preferably for from about 460° F. to about 480° F., to distill off the free fatty acids and flavor materials.

Tysinger et al. teach that care should be exercised in heating the soybeans at temperatures above about 350° F., since the oil will tend to scorch, causing an off taste in the final product and a darker color, and that heating the oil to less than 300° F. will fail to destroy sufficient trypsin inhibitors in the meal. Tysinger et al. also note that the time during which the soybeans are heated is also important, and that heating of the beans to the desired temperature in at least 10 seconds has been found to achieve maximum rupture of the oil cells, and thus maximum extraction of oil from the soybeans, while heating of the beans for longer than about 60 seconds degrades the desirable characteristics of the oil.

The restrictions of the Tysinger et al. process with regard to the desired temperature and time ranges requires careful control of the process and restricts the type of equipment that can be used during mechanical extraction. It would be desirable to have a process that was not constrained by these limitations while still producing a mechanically extracted soybean oil that was suitable for physically refining, thereby achieving an improved soybean oil of the type produced in the earlier Tysinger et al. process.

SUMMARY OF THE INVENTION

Surprisingly, it has been found that soybean oil that is suitable for physical refining can also be obtained by heating the soybeans at a significantly lower temperature for a significantly longer time relative to the temperature and time ranges disclosed by Tysinger et al. Specifically, the present invention comprises the steps of heating soybeans at an elevated temperature of from 220° F. to 260° F. for a period of from about 45 to about 60 minutes, as opposed to the ranges recommended by Tysinger et al. Preferably, the soybeans are heated at a temperature of between about 230° F. and 260° F. for between 50 minutes and 60 minutes. After heating, the oil is mechanically extracted and physically refined to yield extended frylife soybean oil.

Heating of soybeans within broad ranges of temperatures and times which partially overlap the ranges used in the present invention has been disclosed in U.S. Pat. No. 5,225,230 to Seaman et al., issued Jul. 6, 1993. The purpose of Seaman et al. is to produce a soybean meal with an improved protein bypass value, providing better digestion by cattle. However, it has not heretofore been recognized that heating soybeans within selected portions of these disclosed temperatures and ranges, when used in combination with physical refining, can result in soybean oil having improved frylife such as previously achieved only with the conditions described by Tysinger et al.

DETAILED DESCRIPTION OF THE INVENTION

In the practice of the invention, cleaned and dehulled soybeans are heated at a temperature of 220° F. to 260° F. for a period of from 45 to 60 minutes, preferably, between about 230° F. and 260° F. for between 50 minutes and 60 minutes. Uniform heating of the soybeans may be achieved by heating the soybeans in a rotary kiln, such as the rotary kilns produced by The Davenport Company, Davenport, Iowa.

After heating, the soybeans are mechanically pressed, e.g., with a screw extruder, also known as an expeller, to remove up to about 74% to about 76% of the oil from the beans, leaving a soybean meal that includes from about 4% to 8% soybean oil. However, this meal has a substantially higher nutritional value than soybean meal from conventional solvent extraction, with the resultant higher selling prices at least partially offsetting the oil loss. While not being restricted to any particular theory, it is believed that the oil residue left in the meal may include components that contribute to the limited frylife of solvent extracted, caustic refined soybean oil.

The crude soybean oil is then degummed by intimately mixing the crude soybean oil with water, which may contain citric acid or a similar organic acid, to form gums of the hydratable phospholipids, which are then removed from the crude oil, e.g., by centrifuging. The degummed oil is then bleached with bleaching materials, such as clay, silica gel, and if needed for damaged beans, sodium metasilicate. The oil is then vacuum dried and filtered.

At this stage, the oil is a useful product known as refined and bleached oil. However, for many applications it is desirable to further process the oil to remove free fatty acids and components that contribute to the color and flavor of the oil. In the present process, it is possible to remove the free fatty acids without the caustic refining required in prior art processes. Instead, the free fatty acids are removed at the same time as the flavor and color components are removed during physical refining.

As noted earlier, removal of free fatty acids by physical refining has not been feasible due to the large amount of non-hydratable phospholipids in the oil, which degraded under the high temperatures required for physical distillation. In the present process, however, the amount of non-hydratable phospholipids is generally less than 2.0 ppm based on the weight of elemental phosphorous in the compounds as a result of the mechanical extraction. After silica treatment and bleaching, the phosphorous content will be less than 1 ppm. This insignificant amount of phosphorous has no affect on oil flavor or stability.

During the physical refining stage of the invention, free fatty acids and flavor components are removed from the oil by heating the oil in a distillation column to a temperature of from about 450° F. to about 500° F., and preferably for from about 460° F. to about 480° F., to distill off the free fatty acids and flavor materials. By industry standards, the final oil should contain less than about 0.05% free fatty acids.

While the process of the invention is described with reference to soybean oil, it will be appreciated that the process may be suitably used in the extraction and refining of oils from other vegetable seeds in addition of soybeans seed, e.g., rape seed, sunflower seed, corn, etc. The process is also applicable to genetically altered soybeans that yield low linolenic acid.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A process for producing soybean oil from soybeans containing said oil comprising:

a) heating said soybeans at a temperature of from 220° F. to 260° F. for from 45 to 60 minutes;

b) mechanically pressing said soybeans to separate said oil; and c) heating said separated oil at a temperature of up to about 500° F. under a vacuum to remove free fatty acids from said soybean oil.

2. The process of claim 1, wherein said soybeans are heated at a temperature of from about 230° F. to about 260° F. for between 50 and 60 minutes.

3. The process of claim 1, wherein said soybeans are rotated during heating.

4. The process of claim 1, wherein said oil is heated under a vacuum at a temperature of from about 460° F. to about 480° F.

5. The process of claim 1, further including degumming and bleaching said oil following pressing.

6. The process of claim 1, wherein from about 74% to about 76% of the oil is removed from the beans by mechanical pressing.

7. The process of claim 1, wherein said soybean oil contains less than about 0.05% free fatty acids after distilling.

8. A solvent extraction free, caustic refining free, process for producing refined soybean oil from soybeans comprising:

a) heating said soybeans at a temperature of from 220° F. to 260° F. for from 45 to 60 minutes;

b) mechanically pressing said soybeans to separate said oil; and c) heating said oil at a temperature of from about 350° F. to about 500° F. under a vacuum to remove free fatty acids from said soybean oil.

9. The process of claim 8, wherein said soybeans are heated at a temperature of from about 230° F. to 260° F. for between 50 and 60 minutes.

10. The process of claim 8, wherein said oil is heated under a vacuum at a temperature of from about 460° F. to about 480° F.

11. The process of claim 8, further including degumming and bleaching said oil following pressing.

12. The process of claim 8, wherein from about 74% to about 76% of the oil is removed from the beans by mechanical pressing.

13. The process of claim 8, wherein said soybean oil contains less than about 0.05% free fatty acids after distilling.

* * * * *